US010898252B2

(12) United States Patent
Johnson et al.

(10) Patent No.: US 10,898,252 B2
(45) Date of Patent: Jan. 26, 2021

(54) SURGICAL ROBOTIC SYSTEMS FOR BENDING SURGICAL RODS, AND RELATED METHODS AND DEVICES

(71) Applicant: GLOBUS MEDICAL, INC., Audubon, PA (US)

(72) Inventors: Norbert Johnson, North Andover, MA (US); Sritam Parashar Rout, Lowell, MA (US); Weston Healy, Cambridge, MA (US); David Cleary, Somerville, MA (US); Olivier Chappuis, Lutry (CH)

(73) Assignee: Globus Medical, Inc., Audubon, PA (US)

( * ) Notice: Subject to any disclaimer, the term of this patent is extended or adjusted under 35 U.S.C. 154(b) by 56 days.

(21) Appl. No.: 16/183,980

(22) Filed: Nov. 8, 2018

(65) Prior Publication Data

US 2019/0133666 A1 May 9, 2019

Related U.S. Application Data

(60) Provisional application No. 62/583,851, filed on Nov. 9, 2017.

(51) Int. Cl.
*A61B 17/88* (2006.01)
*A61B 17/70* (2006.01)
(Continued)

(52) U.S. Cl.
CPC ...... *A61B 17/8863* (2013.01); *A61B 17/7011* (2013.01); *A61B 17/7013* (2013.01);
(Continued)

(58) Field of Classification Search
CPC ............ A61B 17/8863; A61B 17/7011; A61B 17/7013; A61B 34/30; A61B 2034/2055; A61B 2017/564; B21D 7/00; B21D 7/12
(Continued)

(56) References Cited

U.S. PATENT DOCUMENTS 4,150,293 A    4/1979  Franke
5,246,010 A    9/1993  Gazzara et al.
(Continued)

FOREIGN PATENT DOCUMENTS

JP    2004-9125 A     1/2004
JP    2010-162557 A   7/2010

OTHER PUBLICATIONS

US 8,231,638 B2, 07/2012, Swarup et al. (withdrawn)
(Continued)

*Primary Examiner* — Eduardo C Robert
*Assistant Examiner* — David C Comstock

(57) ABSTRACT

A robotic system may include a robot base and a rod feeding subassembly coupled to the robot base that includes a feeding actuator configured to selectively move a surgical rod. The robotic system may include a brake subassembly coupled to the robot base that includes a brake actuator configured to receive the surgical rod from the rod feeding subassembly, and selectively fix a first portion of the surgical rod with respect to the brake subassembly. The robotic system may include a bending subassembly coupled to the robot base that includes a bending actuator configured to selectively rotate to engage a second portion of the surgical rod and bend the second portion of the surgical rod with respect to the first portion of the surgical rod so that the first portion and the second portion of the surgical rod define a first bend angle.

19 Claims, 14 Drawing Sheets

(51) Int. Cl.
*A61B 34/30* (2016.01)
*B21D 7/00* (2006.01)
*A61B 34/20* (2016.01)
*A61B 17/56* (2006.01)

(52) U.S. Cl.
CPC .............. *A61B 34/30* (2016.02); *B21D 7/00* (2013.01); *A61B 2017/564* (2013.01); *A61B 2034/2055* (2016.02)

(58) Field of Classification Search
USPC .............................. 606/262; 29/34 R, 34 D
See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Sun et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |

(56) References Cited

U.S. PATENT DOCUMENTS

| | | |
|---|---|---|
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |

(56) References Cited

U.S. PATENT DOCUMENTS

| | | |
|---|---|---|
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |

(56) References Cited

U.S. PATENT DOCUMENTS

| | | |
|---|---|---|
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Nasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | Georget et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |

(56) References Cited

U.S. PATENT DOCUMENTS

| | | |
|---|---|---|
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0135793 A1* | 5/2015 | Plummer ............... B21D 11/22 72/311 |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0263646 A1 | 9/2016 | Shazly et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0289491 A1* | 10/2018 | McGahan ............... A61B 34/25 |

OTHER PUBLICATIONS

State of the Art Search for Imaging Devices Used in Conjunction With Surgical Navigation Software for Registering Image Data, performed by Shane Davis of Optimized Intellectual Property Solutions, Nov. 5, 2014, 2 pages.

Search Report for: Automatic Planning of Surgical Screw Position During a Robot Assisted Surgical Procedure by John Johnson, dated Jan. 18, 2018 (GM801), 2 pages.

Search Report for: Breathing Meter for Robotic Assisted Surgery by John Johnson, dated Jan. 22, 2018 (GM802), 3 pages.

Search Report for: Instrument Verification Improvement by John Johnson, dated May 22, 2018 (GM813), 2 pages.

Search Report for: Hammerhead Probe by John Johnson, dated Jul. 3, 2018 (GM816), 2 pages.

Search Report for: Navigation of a Bent Rod by John Johnson, dated Jul. 6, 2018 (GM817), 2 pages.

Search Report for: Large Field of View Cone Beam CT by John Johnson, dated Jul. 12, 2018 (GM818), 2 pages.

Search Report for: Robot Collision Detection by John Johnson, dated Aug. 3, 2018 (GM819), 4 pages.

Search Report for: Implant Trajectory and Tool Planning via Navigated Instrument by John Johnson, dated Aug. 9, 2018 (GM820), 3 pages.

Search Report for: Improved Low-Contrast CBCT Imaging by John Johnson, dated Aug. 6, 2018 (GM821), 3 pages.

Allowed Claims, showing Amendments to the claims for U.S. Patent Application Publication No. 2009/0185655, 7 pages.

Allowed Claims, showing Amendments to the claims for U.S. Patent Application Publication No. 2016/0005194, 4 pages.

Patent Search for CBCT-fluoroscopy-radiography, Mar. 2, 2018.

* cited by examiner

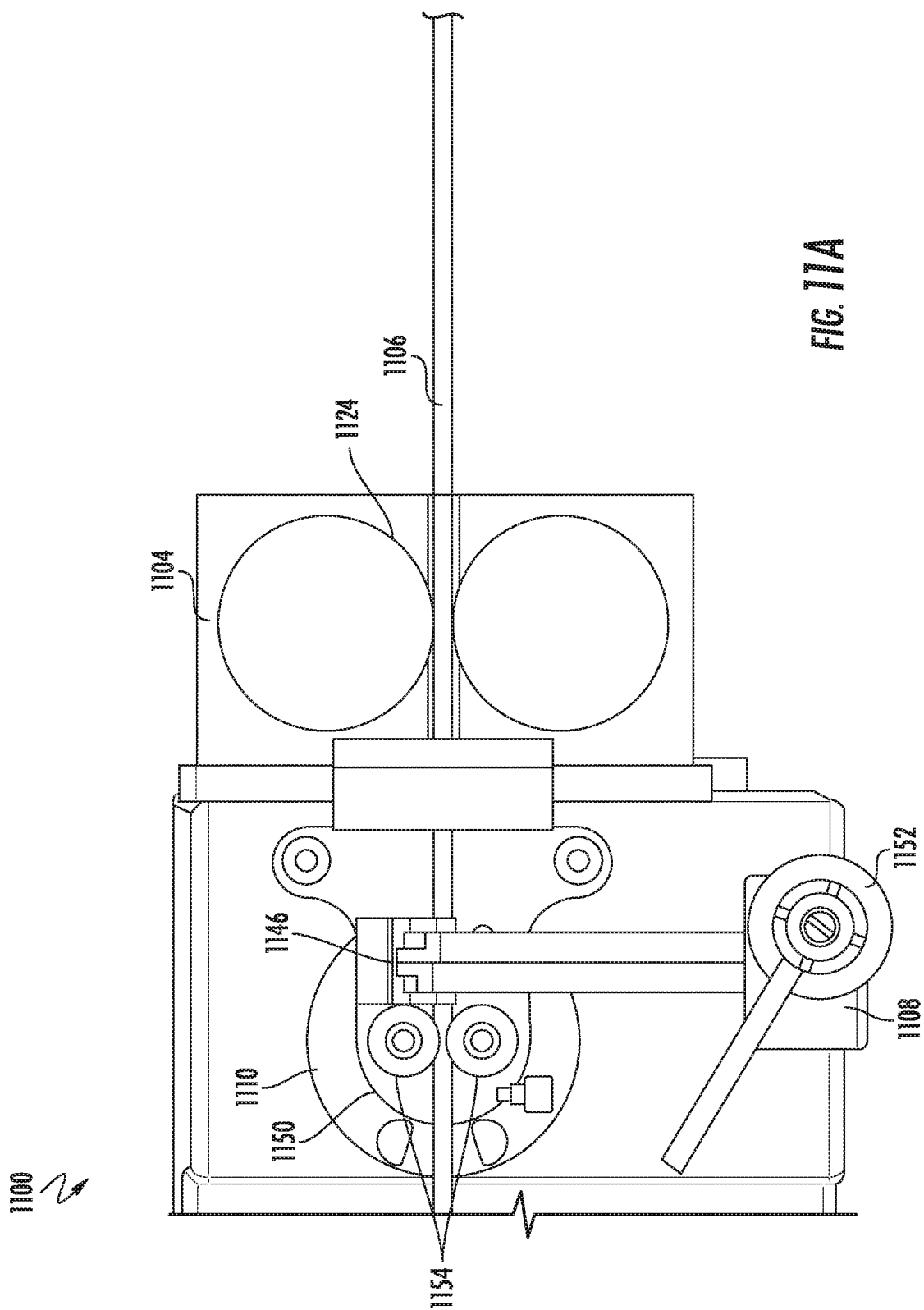

SURGICAL ROBOTIC SYSTEMS FOR BENDING SURGICAL RODS, AND RELATED METHODS AND DEVICES

This application is a non-provisional application which claims priority to provisional application Ser. No. 62/583,851 filed on Nov. 9, 2017, which is incorporated in its entirety herein.

FIELD

The present disclosure relates to medical devices, and more particularly, surgical robotic systems for bending surgical rods, and related methods and devices.

BACKGROUND

Spinal fusion is a surgical procedure used to correct deformity of the spine by fusing together the painful part of the spine in order to restrict its motion and relieve painful symptoms. Spinal fusion surgery is commonly utilized to treat abnormal spinal curvatures, such as scoliosis and abnormal kyphosis, for example, degenerative disc diseases, spondylolisthesis, trauma resulting in spinal nerve compression, vertebral instability caused by infections or tumors, and other conditions.

Fusion surgery may include the placement of rods and screws using instrumentation and/or the placement of bone graft in between the vertebrae. During surgery, the surgeon may correct the deformity of the spine so as to ensure that the radiographic parameters of the spine in both the sagittal and coronal plane fall within clinically accepted values. While doing so the surgeon fixes the corrected spine into place using metallic rods. The rods need to conform to the shape of the spine and hence need to be bent accordingly.

Currently, devices such as French bender and power bender are utilized in the operation room in order to bend the rods to the desired curvature. However, these devices require cumbersome manual processes to operate. In addition, use of these devices to bend the rod may also introduced notches on the rod, which may decrease the rod's fatigue life.

SUMMARY

According to some embodiments of inventive concepts, a robotic system for automatically bending a surgical rod is disclosed. The robotic system includes a robot base and a rod feeding subassembly coupled to the robot base. The rod feeding subassembly includes a feeding actuator configured to retain a surgical rod therein, and selectively move the surgical rod in a direction parallel to a longitudinal axis of the surgical rod. The robotic system further includes a brake subassembly coupled to the robot base. The brake subassembly includes a brake actuator configured to receive the surgical rod from the rod feeding subassembly, and selectively fix a first portion of the surgical rod with respect to the brake subassembly. The robotic system further includes a bending subassembly coupled to the robot base. The bending subassembly includes a bending actuator configured to selectively rotate about a first rotational axis perpendicular to the longitudinal axis of the surgical rod. Rotating the bending actuator causes the bending actuator to engage a second portion of the surgical rod and bend the second portion of the surgical rod with respect to the first portion of the surgical rod so that the first portion and the second portion of the surgical rod define a first bend angle.

According to some other embodiments of inventive concepts, a method of operating a robotic system is disclosed. The method includes selectively operating a rod feeding subassembly, including retaining a surgical rod in the rod feeding subassembly. Operating the rod feeding subassembly further includes causing a feeding actuator of the rod feeding subassembly to selectively move the surgical rod in a direction parallel to a longitudinal axis of the surgical rod. The method further includes selectively operating a brake subassembly, including receiving the surgical rod in the brake feeding subassembly from the rod feeding subassembly. Operating the brake subassembly further includes causing a brake actuator of the brake subassembly to selectively fix a first portion of the surgical rod with respect to the brake subassembly. The method further includes selectively operating a bending subassembly, including causing a bending actuator of the bending subassembly to selectively rotate about a first rotational axis perpendicular to the longitudinal axis of the surgical rod. Rotating the bending actuator causes the bending actuator to engage a second portion of the rod and bend the second portion of the rod with respect to the first portion of the surgical rod so that the first portion and the second portion of the surgical rod define a first bend angle.

Other methods and related surgical systems, and corresponding methods and computer program products according to embodiments of the inventive subject matter will be or become apparent to one with skill in the art upon review of the following drawings and detailed description. It is intended that all such surgical systems, and corresponding methods and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIGS. 11A and 11B illustrate components of a bending robot according to another alternative embodiment.

DETAILED DESCRIPTION

Figure 1:
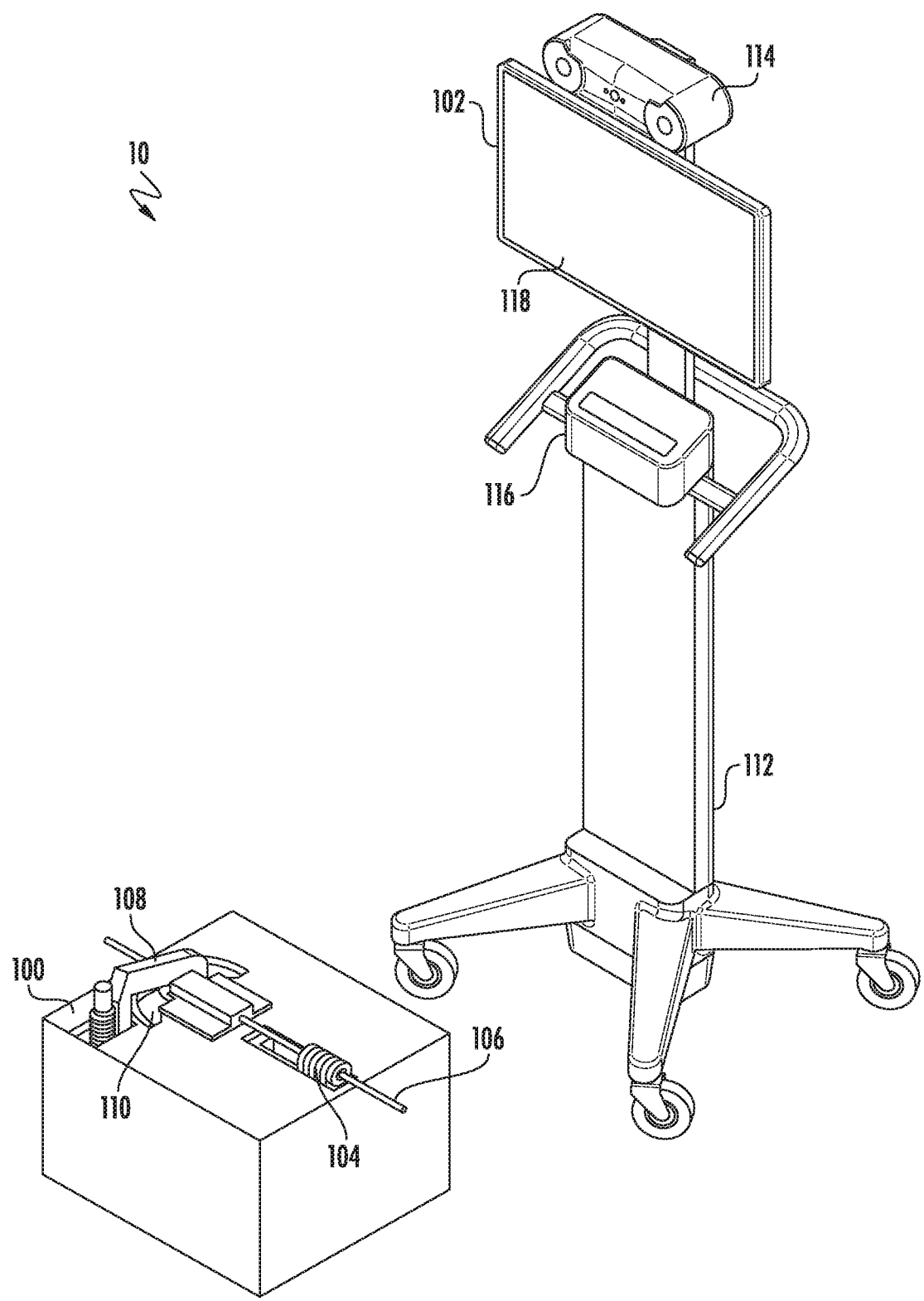
FIG. 1 illustrates a view of a robotic bending system for automatically bending a surgical rod, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Referring now to FIG. 1, a view of a robotic bending system 10 for automatically bending a surgical rod intraoperatively is illustrated according to some embodiments. The bending system 10 of FIG. 1 includes a bending robot 100 and may also include a controller unit 102 for controlling and/or monitoring the operation of the bending robot 100 and/or other components or devices. The bending robot 100 includes a rod feeding subassembly 104 for receiving, feeding, and rotating a surgical rod 106, a brake subassembly 108 for retaining a first portion of the surgical rod 106 at a particular position, and a bending subassembly 110 for bending a second portion of the surgical rod 106 with respect to the first portion of the surgical rod 106 to define a bend angle between the first and second portions of the surgical rod 106. By feeding and rotating additional sections of the surgical rod 106, additional portions of the surgical rod can be bent to form a number of different shapes suitable for use in spinal fusion surgery or other procedures.

In this example, the controller unit 102 may include a controller base 112 and a plurality of components, which may be in communication with each other and/or components of the bending robot 100, as desired. For example, the controller unit may include a camera 114 for monitoring the bending robot and/or other aspects of the surgery or procedure, an input device 116 for receiving instructions from a user before or during the procedure, and a display device 118 for providing visual information to a user before or during the procedure. The robot 100 and/or controlled unit 102 may include one or more processor circuits (not shown) for executing machine-readable instructions to operate components of the bending robot 100 or other components or devices.

Figure 2:
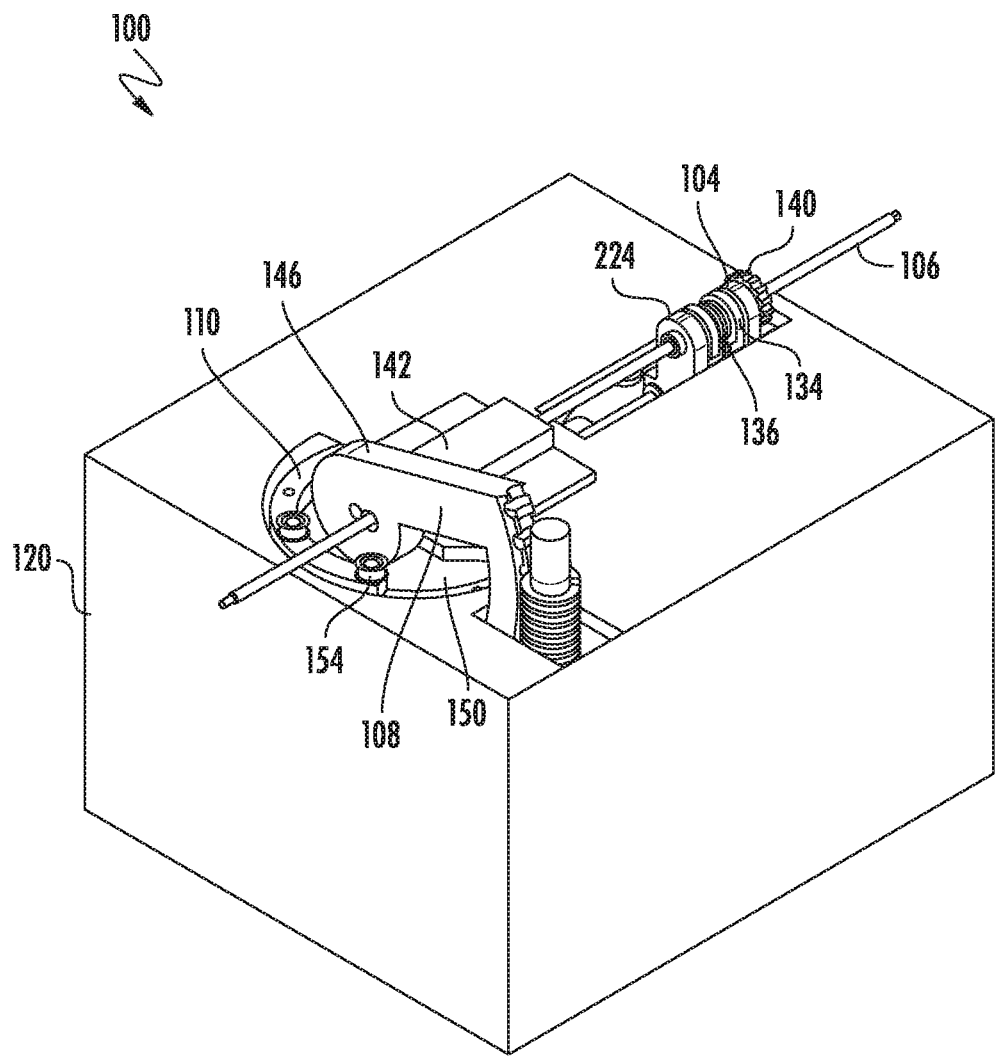
FIG. 2 illustrates a view of a bending robot of the robotic bending system of FIG. 1, according to some embodiments.

Referring now to FIG. 2, a more detailed view of the bending robot 100 of FIG. 1 is illustrated, according to some embodiments. As shown in FIG. 2, the bending robot 100 includes a robot housing 120 that is part of a robot base for housing components of the rod feeding subassembly 104, brake subassembly 108, bending subassembly 110, and other components. The rod feeding subassembly 104 includes a rod feeding actuator 124 configured to retain a surgical rod 106 therein, selectively move the surgical rod 106 in a direction parallel to a longitudinal axis of the surgical rod 106, and selectively rotate the surgical rod about the longitudinal axis of the surgical rod 106. The rod feeding actuator 124 includes an actuator spindle 134 with a pulley cable 136 wound therearound, and a retaining ring 140 for retaining and aligning the surgical rod 106. In this example, the retaining ring 140 is sized to hold the surgical rod 106 in place by friction, and to allow the rod to slide through the ring when an appropriate amount of force is applied to the surgical rod 106. The retaining ring 140 in this example may be selectively replaced with a differently sized retaining ring to accommodate a surgical rod having a different diameter. As will be discussed below, a pulley subassembly (not shown) selectively advances and rotates the surgical rod 106 to position the surgical rod 106 in a correct location and orientation with respect to the brake subassembly 108 and the bending subassembly 110. It should also be understood that, while this embodiment uses a pulley subassembly, other types of feeding actuator linkages may be used to transfer power from one or more motors to move and/or rotate the rod feeding actuator 124.

The brake subassembly 108 includes a brake housing 142 and a brake actuator 146 configured to receive the surgical rod 106 from the rod feeding subassembly 104, and selectively fix a first portion of the surgical rod 106 with respect to the brake subassembly 108. In this embodiment, after the brake actuator 146 fixes the surgical rod 106, the rod feeding subassembly 104 moves longitudinally back to its original position and may advance and/or rotate the surgical rod 106 further after the brake actuator 146 is released.

While the brake actuator 146, is engaged, the bending subassembly 110 includes a bending actuator 150 that selectively rotate about a first rotational axis perpendicular to the longitudinal axis of the surgical rod 106 to engage a second portion of the surgical rod 106 and bend the second portion of the surgical rod 106 with respect to the first portion of the surgical rod 106 so that the first portion and the second portion of the surgical rod 106 define a first bend angle. To prevent notching of the surgical rod 106 during the bending process, a pair of roller bearings 154 positioned on either side of the surgical rod 106 form the engagement points between the surgical rod 106 and the bending actuator 150 during the bending process.

Figure 3:
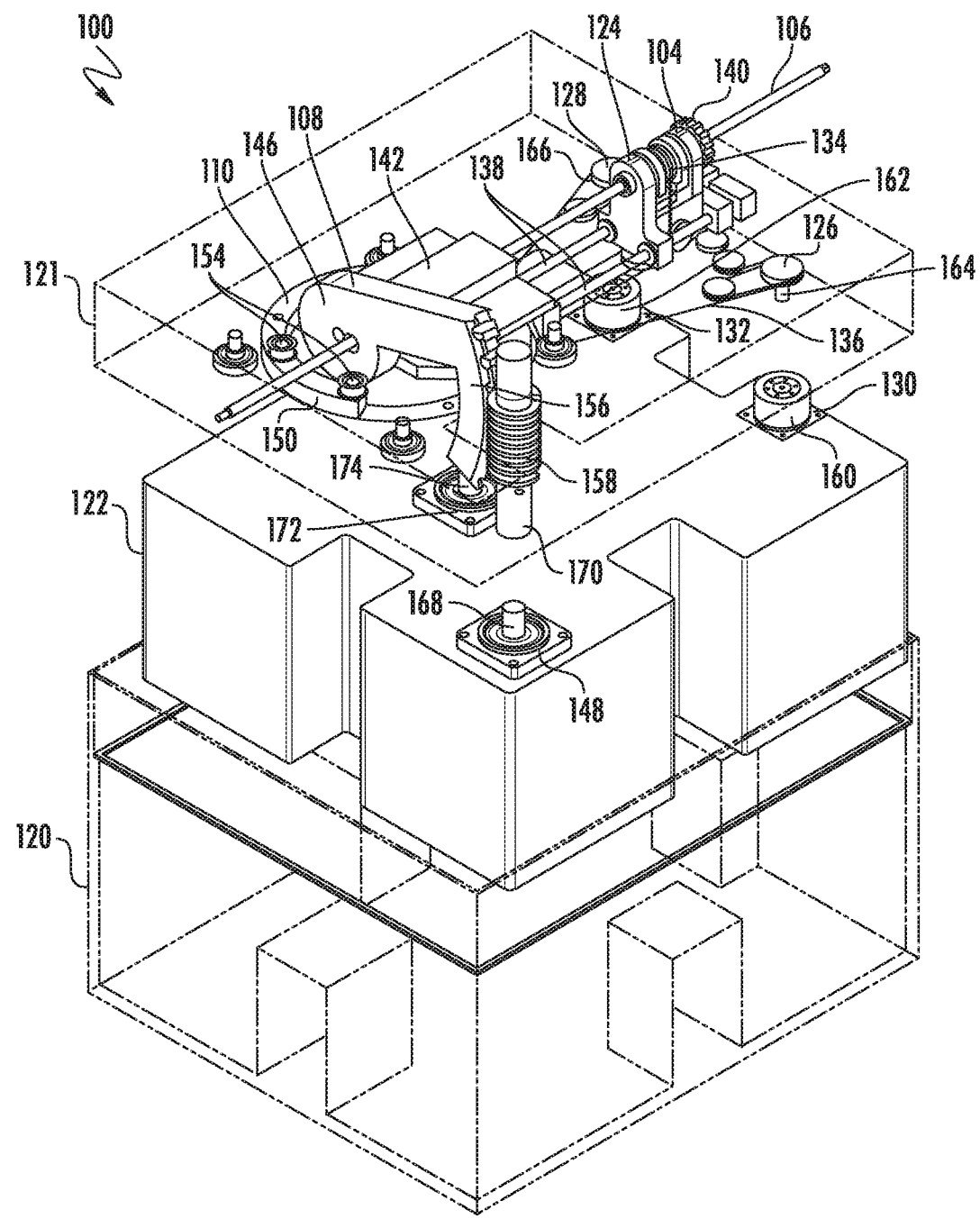
FIG. 3 illustrates a partially disassembled view of the bending robot of FIG. 2, according to some embodiments.

Referring now to FIG. 3, a partially disassembled view of the bending robot 100 of FIG. 2 is illustrated according to some embodiments. In this example, a mechanical housing 121 include mechanical components of the rod feeding subassembly 104, brake subassembly 108, and bending subassembly 110, and a motor housing 122 includes additional components of the bending robot 100, including a first feeding actuator motor 130, a second feeding actuator motor 132, a brake actuator motor 148, a bending actuator motor 172, and/or additional internal mechanical and/electrical components such as additional linkages and/or electronic processor circuits or other circuits. For example, in some examples a memory coupled to a processor circuit may include machine-readable instructions that, when executed by the processor circuit, cause the processor circuit to cause the rod feeding subassembly 104 to selectively move the surgical rod and selectively rotate the surgical rod 106, cause the brake subassembly 108 to selectively fix the first portion of the surgical rod, and/or cause the bending subassembly 110 to selectively rotate about the first rotational axis to engage the second portion of the surgical rod 106 and bend the second portion of the surgical rod with 106 respect to the first portion of the surgical rod 106.

The mechanical housing 121 is configured to be removably coupled to the motor housing 122 so that the first and second feeding actuator motors 130, 132, brake actuator motor 148, and bending actuator motor 172 can selectively operate the rod feeding subassembly 104, brake subassembly 108, and bending subassembly 110, respectively. In this example, the mechanical housing 121 does not include any electrical or electronic components that could be damaged by conventional preoperative or intraoperative sterilization techniques, such as autoclaving, high-temperature steam sterilization, chemical sterilization, or other techniques. Thus, by disposing the non-sterile motor housing 122 in the sterile robot housing 120, and removably coupling the sterile mechanical housing 121 onto the motor housing 122, intraoperative sterility can be maintained without needing to expose the electrical and/or electronic components of the bending robot 100 to harsh sterilization techniques that may damage these components and may reduce the useful life of these components.

As shown in FIG. 3, the rod feeding subassembly includes a first pulley subassembly 126 configured to engage and be driven by the first feeding actuator motor 130, and a second pulley subassembly 128 configured to engage and be driven by the second feeding actuator motor 132. A pulley cable 136 is wound around first pulley subassembly 126 and the second pulley subassembly 128, as well as the actuator spindle 134 of the rod feeding actuator 124. The first pulley subassembly 126 includes a first pulley transmission input 160 that matingly engages with a first pulley transmission output 164 that is driven by the first feeding actuator motor 130. The first pulley subassembly 126 also includes a second pulley transmission input 162 that matingly engages with a second pulley transmission output 166 that is driven by the second feeding actuator motor 132.

In this embodiment, the directions of rotation of the first feeding actuator motor 130 and the second feeding actuator motor 132 determine the direction or movement and/or rotation of the surgical rod 106. For example, to move the rod feeding actuator 124 in a longitudinal direction along a longitudinal rail subassembly 138 toward the brake subassembly 108 and bending subassembly 110, the first feeding actuator motor 130 rotates counterclockwise and the second feeding actuator motor 132 rotates clockwise. Similarly, to move the rod feeding actuator 124 in a longitudinal direction along the longitudinal rail subassembly 138 away from the brake subassembly 108 and bending subassembly 110, the first feeding actuator motor 130 rotates clockwise and the second feeding actuator motor 132 rotates counterclockwise. To rotate the actuator spindle 134 in a clockwise direction, the first feeding actuator motor 130 rotates clockwise and the second feeding actuator motor 132 also rotates clockwise. To rotate the actuator spindle 134 in a counterclockwise direction, the first feeding actuator motor 130 rotates counterclockwise and the second feeding actuator motor 132 also rotates counterclockwise.

The brake actuator 146 is configured to engage and be driven by the brake actuator motor 148. The brake actuator 146 includes a worm gear 158 having a brake transmission input 168 that matingly engages with a brake transmission output 170 that is driven by the brake actuator motor 148. Driving the worm gear 158 causes a brake gear arm 156 to engage and/or disengage the brake actuator 146 to selectively fix or release the surgical rod 106. In this example, selective operation of the brake actuator motor 148 in a first rotational direction when the brake actuator 146 is in a neutral position causes the brake gear arm 156 to move the brake actuator 146 from the neutral position to an engaged position to selectively fix the first portion of the surgical rod 106 with respect to the brake subassembly 108. Similarly, selective operation of the brake actuator motor 148 in a second rotational direction opposite the first rotational direction when the brake actuator 146 is in the engaged position causes the brake gear arm 156 to move the brake actuator 146 from the engaged position to the neutral position to selectively release the surgical rod 106. In this example, the brake subassembly 108 is a brake and cutting subassembly that further includes an internal blade mechanism (not shown), wherein selective operation of the brake actuator motor 148 in the second rotational direction when the brake actuator 146 is in the neutral position causes a blade of the internal blade mechanism to cut the surgical rod 106. In this example, two internal plates may be slid apart in a reverse scissoring motion, introducing tension to the rod in two different directions and trimming the excess. It should also be understood that an alternative or additional brake actuator linkage may be used in place of or in addition to the worm gear 158 and brake gear arm 156 of the brake subassembly 108.

Similar to the rod feeding subassembly 104 and the brake subassembly 108, the bending actuator 150 of bending subassembly 110 includes a bending transmission input (not shown) that matingly engages with a bending transmission output 174 that is driven by the bending actuator motor 172, and that transfers power from the bending actuator motor 172 through a bending actuator linkage (not shown) to drive the bending actuator 150. Thus, when the sterile mechanical housing 121 is removably coupled to the motor housing 122 in the sterile robot housing 120, the bending robot 100 is able to automatically bend the surgical rod 106 in real-time in a sterile, intraoperative environment. Following each bend, the previously fixed portion of the surgical rod 106 may be advanced and/or rotated by the rod feeding subassembly 104 and another portion may be fixed by the brake subassembly 108. The bending subassembly 110 then bends the previously fixed portion of the surgical rod 106, and so on, until the rod is bent to a desired shape and can be cut and used as part of the spinal fusion surgery or other procedure.

Figure 4:
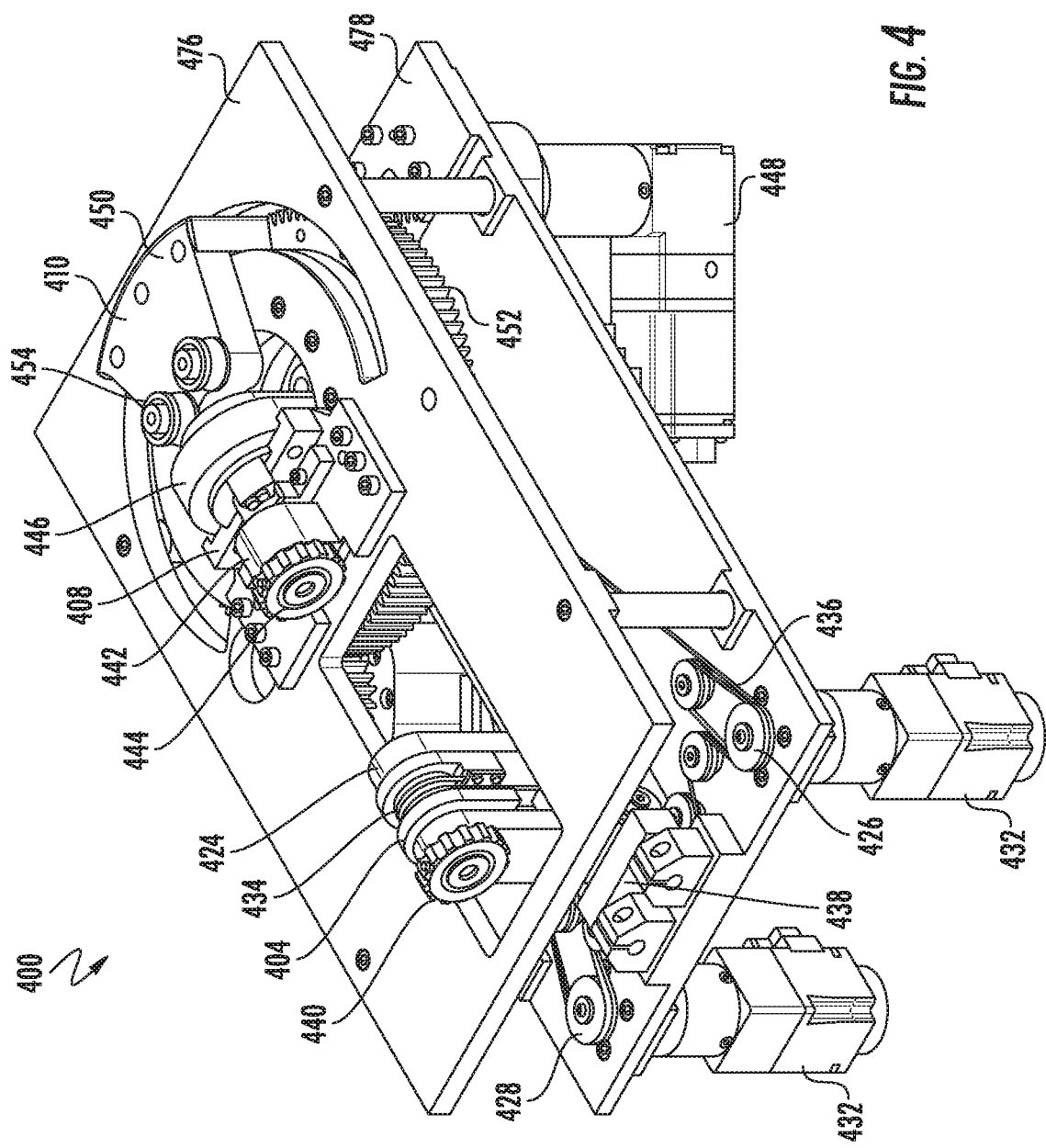
FIG. 4 illustrates an internal view of components of a bending robot according to an alternative embodiment.
Figure 5:
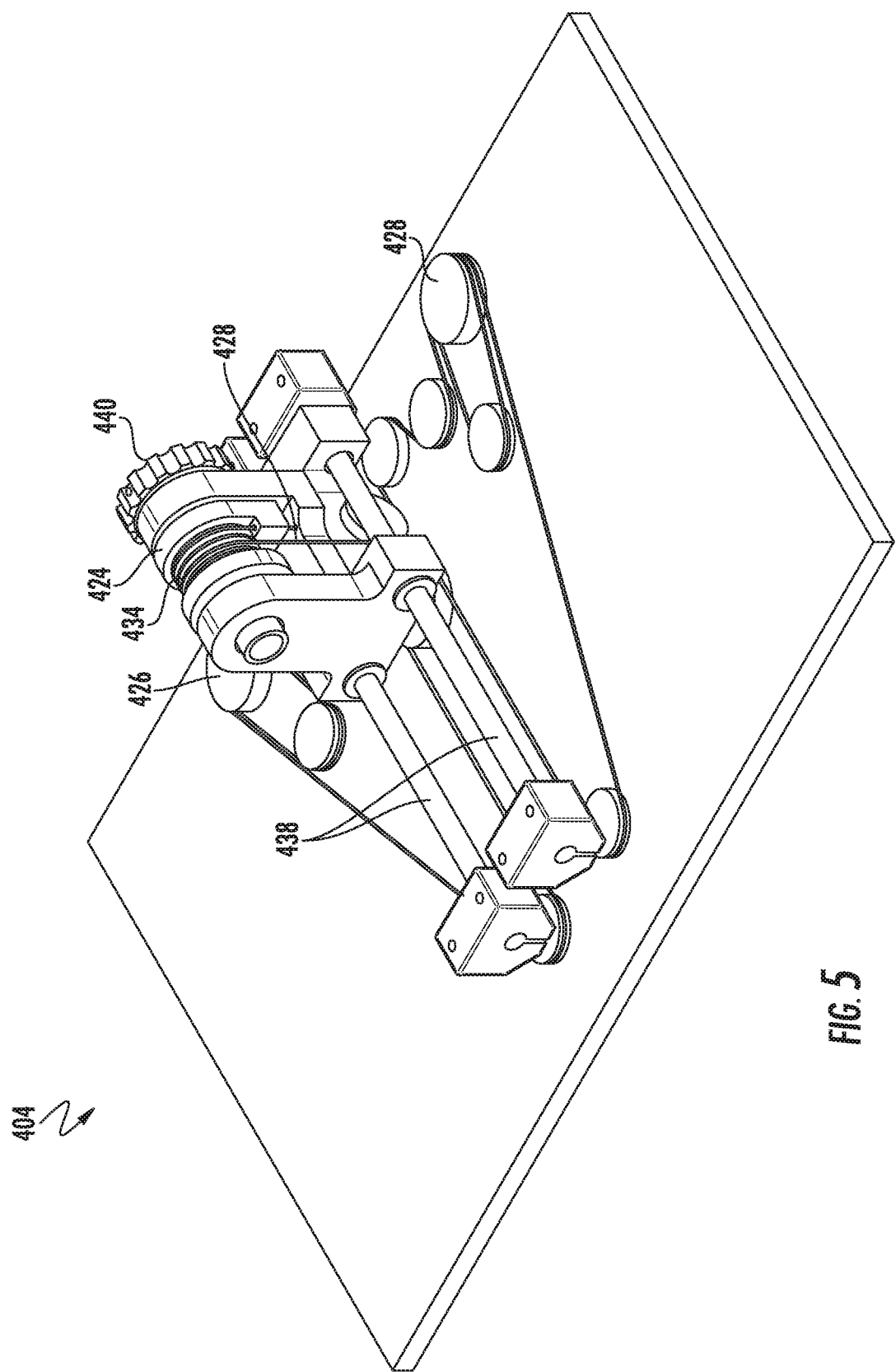
FIG. 5 illustrates components of a rod feeding subassembly of the bending robot of FIG. 4, according to some embodiments.

Referring now to FIGS. 4-7, components of a bending robot 400 according to an alternative embodiment are illustrated. As shown by FIG. 4, the bending robot 400 in this embodiment includes a rod feeding subassembly 404, a brake and cutting subassembly 408, and a bending subassembly 410. As shown by FIGS. 4, and 5, the rod feeding subassembly 404 includes a rod feeding actuator 424 that is selectively longitudinally movable and rotatable via a first pulley subassembly 426 and second pulley subassembly 428. A first feeding actuator motor 430 and a second feeding actuator motor 432 transfer power through the first pulley subassembly 426 and second pulley subassembly 428 via a pulley cable 436 to move the actuator spindle 434 along a longitudinal rail subassembly 438 and rotate the actuator spindle. The actuator spindle 434 includes a removable retaining ring 440 for retaining and aligning the surgical rod (not shown) therein.

Figure 6:
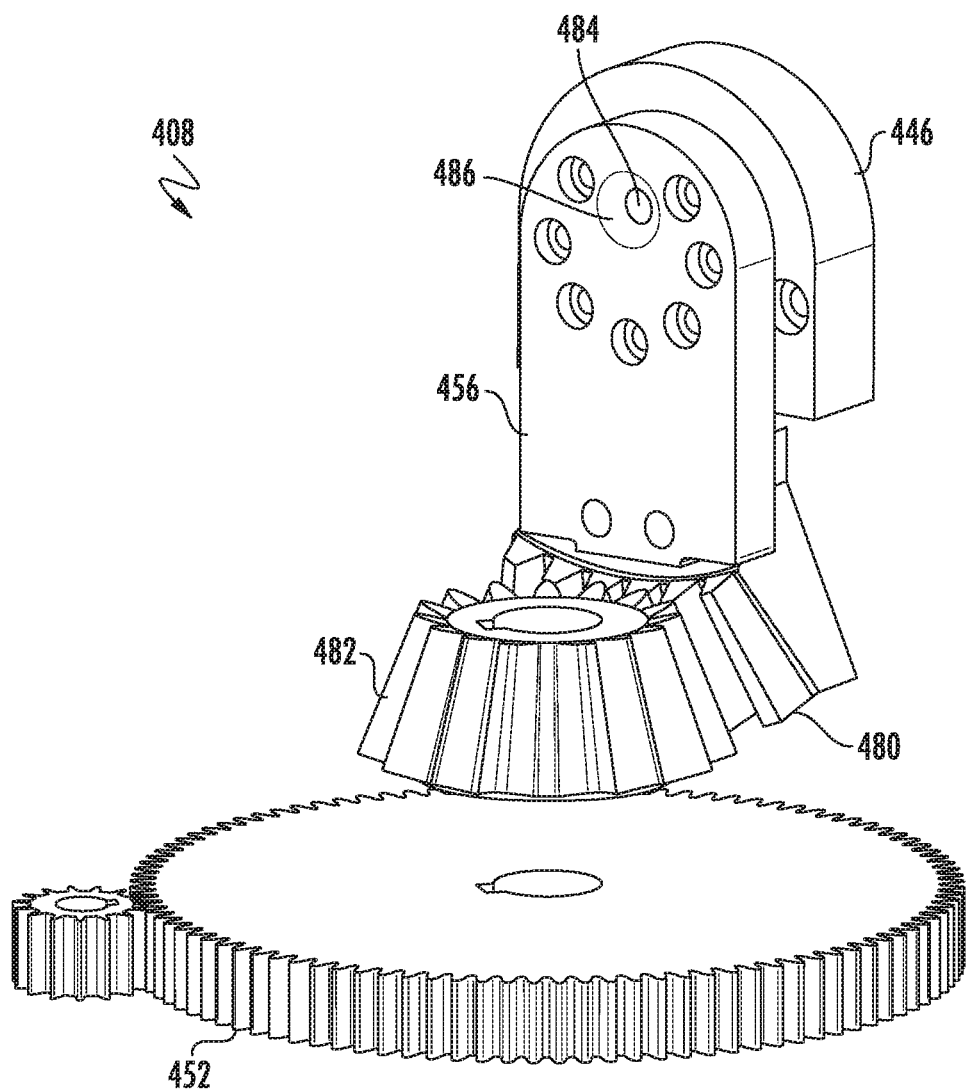
FIG. 6 illustrates components of a brake and cutting subassembly of the bending robot of FIG. 4, according to some embodiments.

As shown by FIG. 4, the brake and cutting subassembly 408 includes a brake housing 442 having a retaining ring 444 similar to the retaining ring 440 of the rod feeding subassembly 404, for receiving and aligning the surgical rod. A brake actuator 448 is controlled by a brake actuator motor 448 to selectively fix and/or release the surgical rod. As shown by FIG. 6, the brake actuator 446 includes a brake gear subassembly including a brake gear 482. In this example, the brake gear is coaxial with, but independently rotatable with respect to, the main gear of the bending gear subassembly 452. This arrangement is to conserve internal space, but it should be understood that other mechanical arrangements may be used to achieve the same or similar functionality. In this example, rotating the brake gear 482 causes the brake gear arm 456 to rotate in a first direction from a neutral position, wherein the surgical rod can be freely moved and rotated with respect to through-hole 484, to an engaged position, wherein the brake gear arm rotates to compress the surgical rod within the through-hole and fix the surgical rod in place. In this embodiment, rotating the brake arm from the neutral position in an opposite direction causes a blade of an internal blade mechanism (not shown) to cut the surgical rod.

Figure 7:
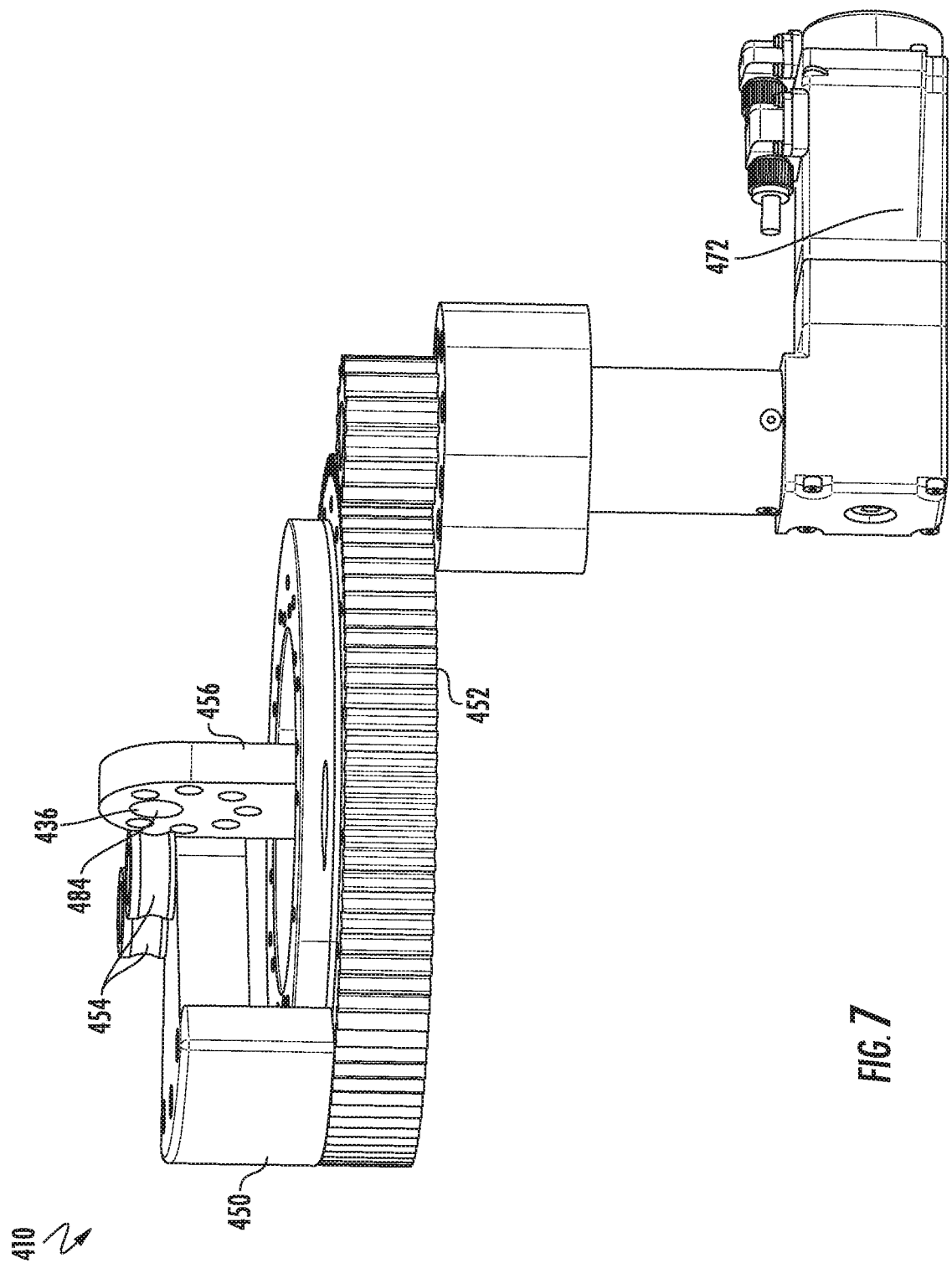
FIG. 7 illustrates components of a bending subassembly of the bending robot of FIG. 4, according to some embodiments.

Referring now to FIG. 7, the bending subassembly 410 includes a bending actuator 450 controlled by a bending actuator motor 472 via a bending gear subassembly 452. A pair of roller bearings 454 are configured to engage the surgical rod when the bending actuator 450 is rotated to bend the surgical rod to a predetermined bend angle.

Figure 8:
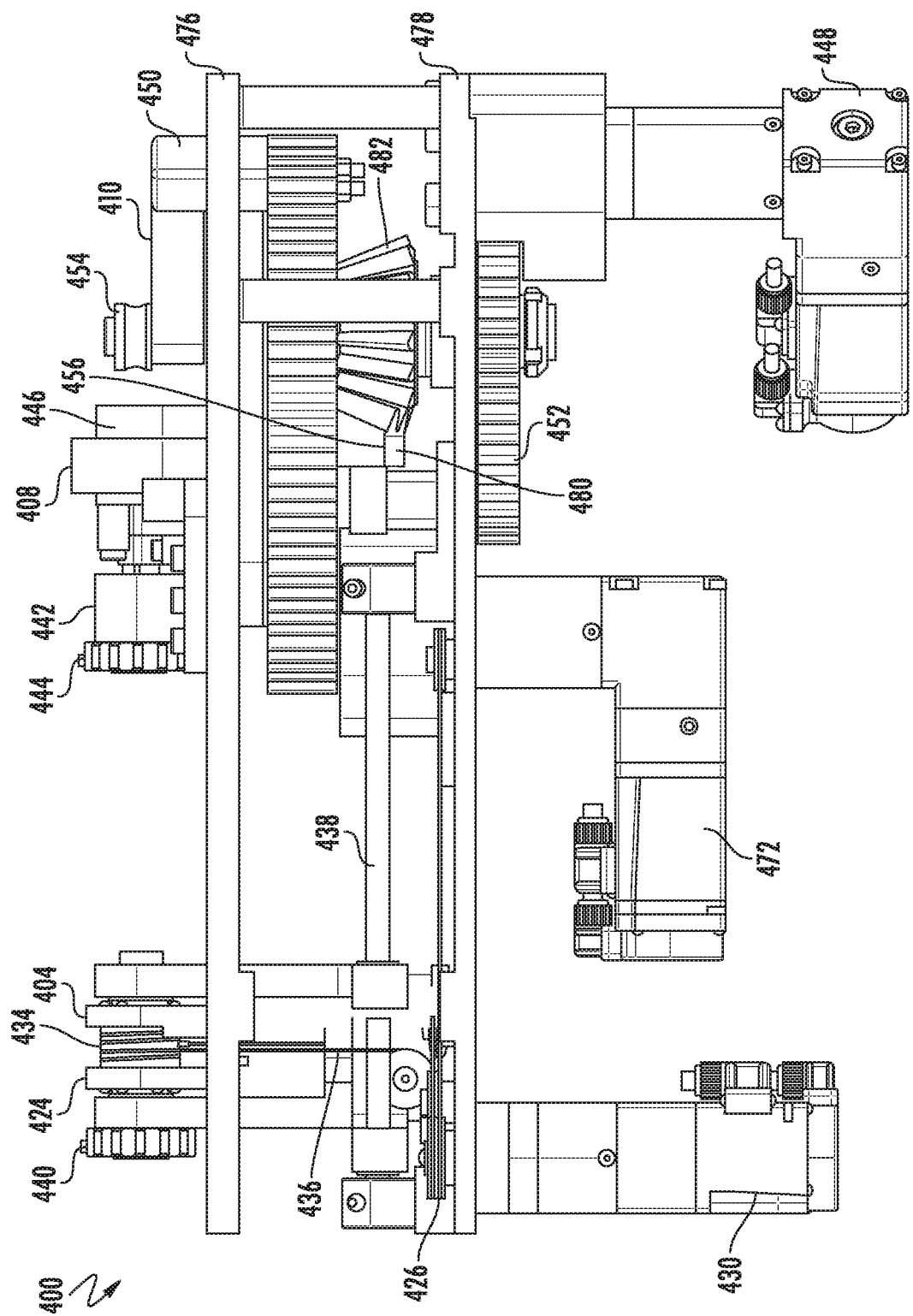
FIG. 8 illustrates a side view of the components of the bending robot of FIG. 4, according to some embodiments.

FIG. 8 illustrates a side view of the components of the bending robot 400 of FIG. 4. As shown by FIG. 8, the components of the bending robot 400 in this example are coupled to an upper support structure 476 and a lower support structure 478 coupled to and spaced apart from the upper support structure 476, to provide structural support for the components of the bending robot 400 while allowing for easier access to the components of the bending robot 400 for maintenance and repair, for example.

Many techniques are available for sterilizing and preventing contamination of a surgical rod being bent in an intraoperative environment. For example, the embodiment of FIGS. 2 and 3 includes a removable mechanical housing 121 that can be completely sterilized using conventional sterilization techniques without risking damage to the electrical or other components of the separate motor housing 122. In another example illustrated in FIG. 9, a bending robot 900 includes a rod feeding subassembly 904 and a bending subassembly 910 for feeding, rotating and bending a surgical rod 906. In this example, the bending robot 900 includes integrated computing components, including an integrated display 918, for controlling the bending robot 900.

Figure 9:
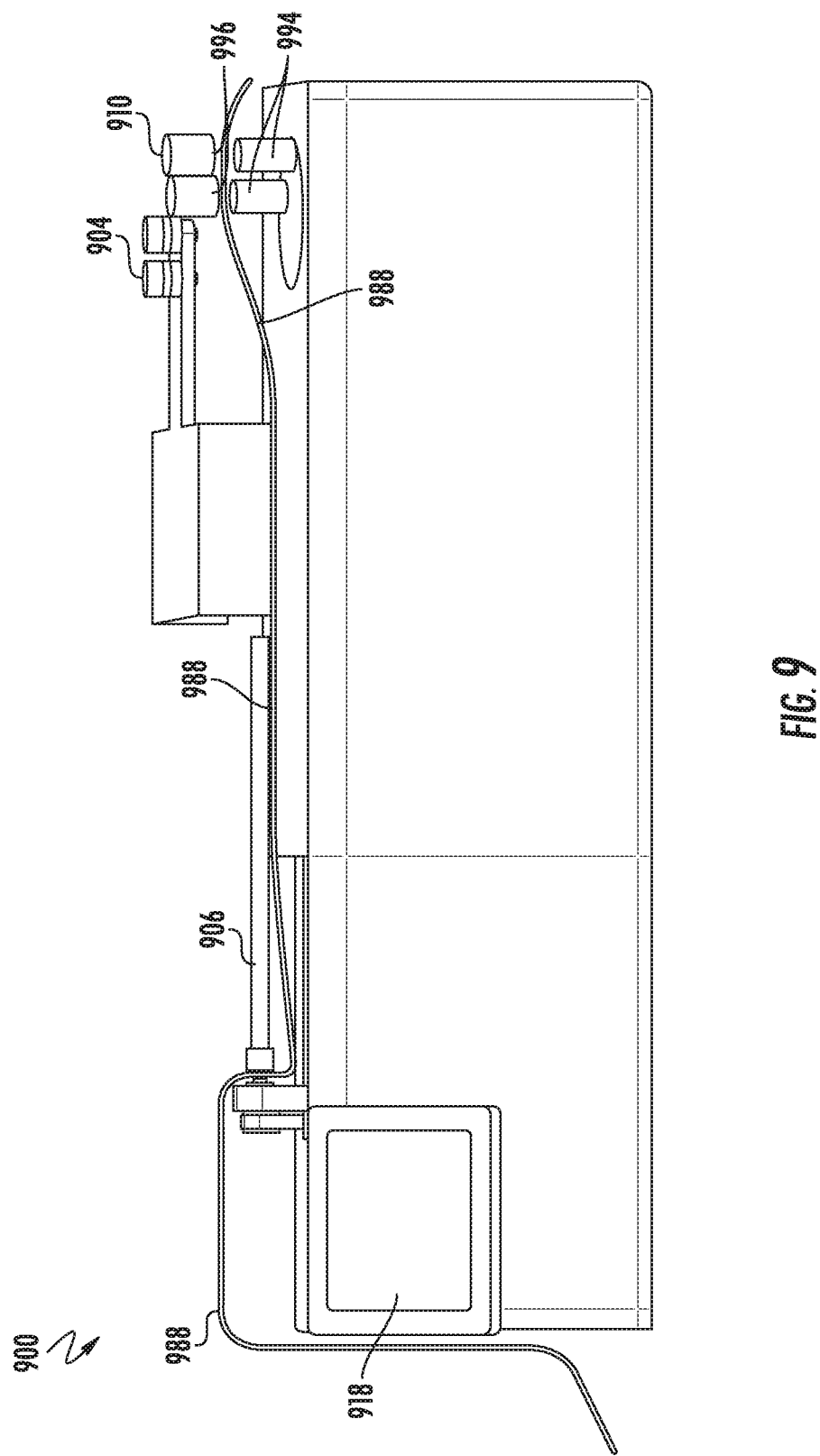
FIG. 9 illustrates components of a rod feeding subassembly for a bending robot according to another alternative embodiment.

In the embodiment of FIG. 9, a sterile drape 988 may cover the non-sterilized components of the bending robot 400, with sterilized components being coupled to the non-sterilized components via magnetic connectors 990, 994 of the sterilized components matingly coupling to complementary magnetic connectors 992, 996 (e.g., male-female connections) of the non-sterilized components, with motion of the components being transferred through the drape 988. While magnetic connections are used in this embodiment, it should be understood that other connections, such as a tight-fit mechanism that allows for transferring mechanical motion without compromising the integrity of the drape 988, may be used. For example, in this and other embodiments, the rotatable components do not require a range of motion of more than 180 degrees. Because of this relatively small range of rotation, using a tight fit mechanism is possible without tearing or otherwise unduly straining the drape 988.

Figure 10A:
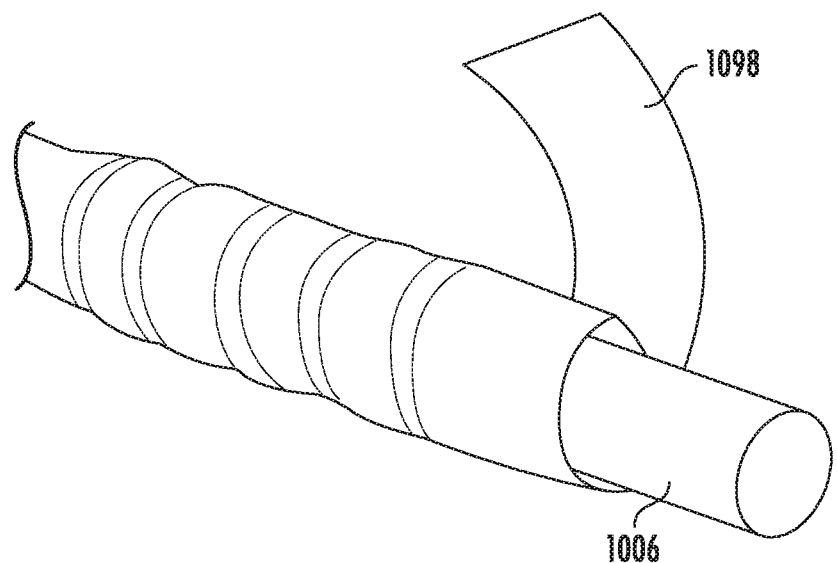
FIGS. 10A-D illustrate surgical rods having removable sterile sleeves, according to some embodiments.

In some embodiments, a sterile surgical rod may be sealed within a sterile sleeve or wrap, which is then bent intraoperatively in a non-sterile environment. In this regard, FIGS. 10A-D illustrate surgical rods having removable sterile sleeves as illustrated, according to some embodiments. Referring to FIG. 10A, a sterile surgical rod 1006 is wrapped in a spiral sterile wrap 1098 material. Following bending of the surgical rod 1006, the spiral sterile wrap 1098 may be removed and the sterile surgical rod 1006 may be delivered into the sterile intraoperative environment.

Figure 10B:
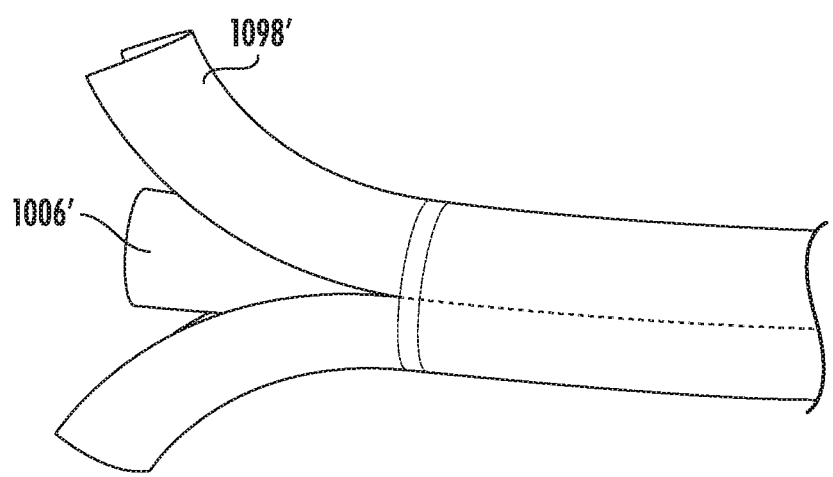
Figure 10C:
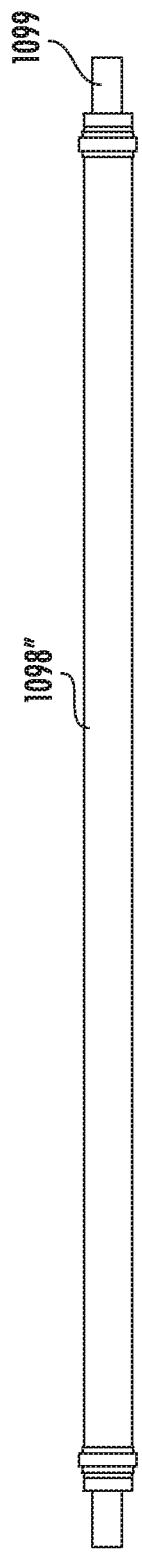
Figure 10D:
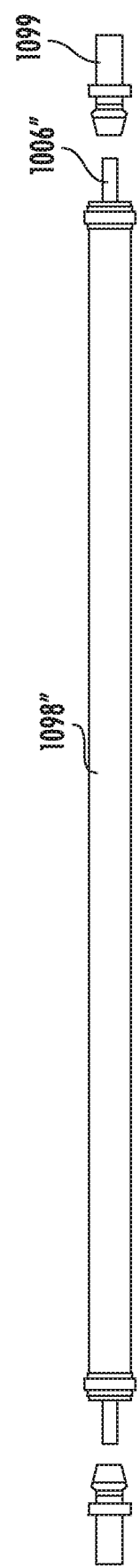

Similarly, FIG. 10B illustrates another sterile surgical rod 1006' having a sterile sleeve 1098' that may be peeled away from the sterile surgical rod 1006' following bending of the sterile surgical rod 1006'. FIGS. 10C and 10D illustrate a sterile surgical rod 1006" disposed in a sterile flexible shaft 1098", which is sealed at either end by removable caps 1099. A bending robot in a non-sterile environment may be configured to bend the flexible shaft 1098", thereby bending the sterile surgical rod 1006" within the flexible shaft 1098" without contacting or contaminating the sterile surgical rod 1006".

Following the bending process, the sterile surgical rod 1006" may be removed from the flexible shaft 1098" and delivered into the sterile intraoperative environment. In these and other embodiments, the coverings for the sterile surgical rods 1006, 1006', 1006" may have a uniform outer diameter, so that different surgical rod diameters may be used without the need for a bending robot to adjust to different outside diameters of the respective coverings.

Figure 11B:
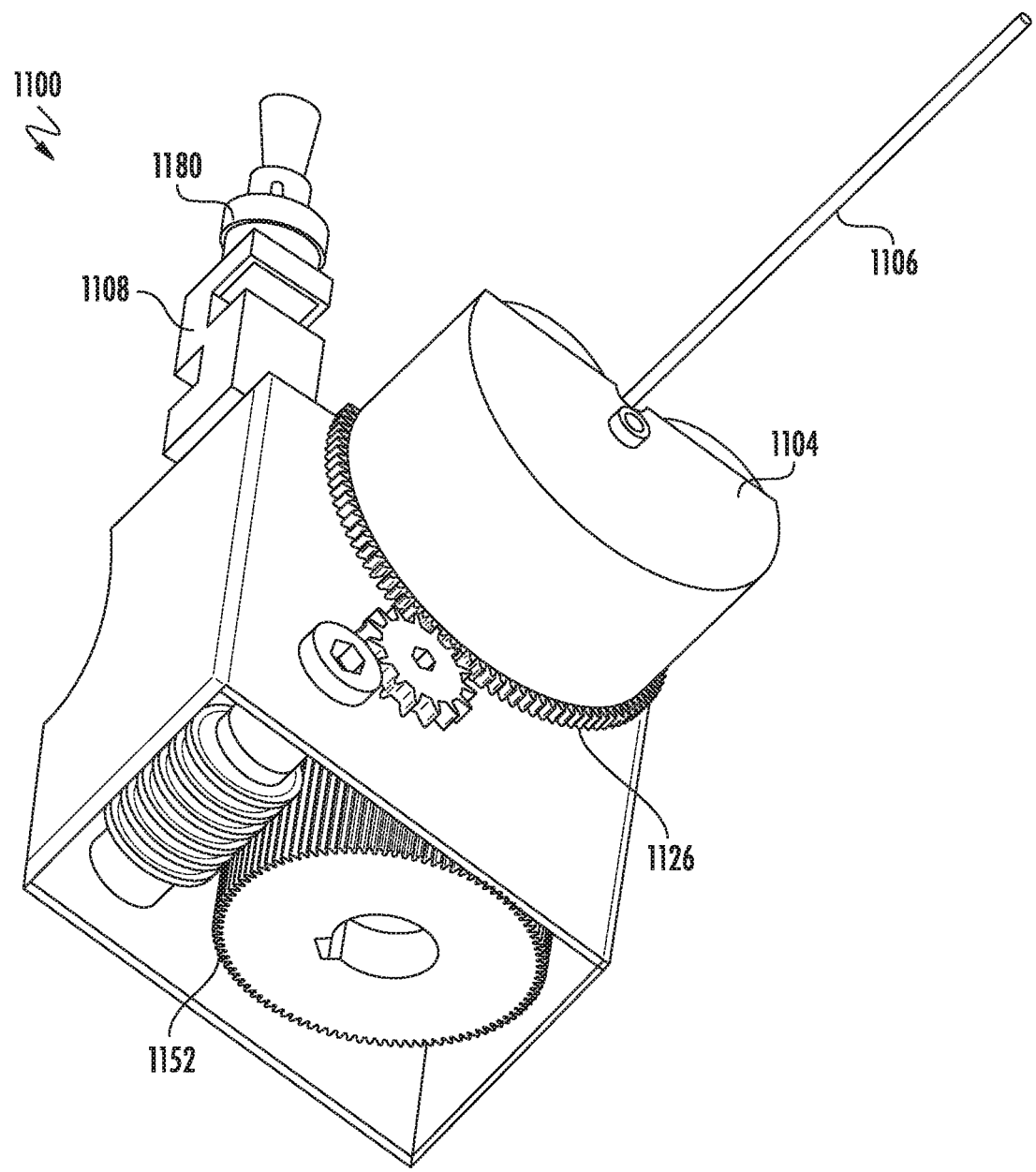

FIGS. 11A and 11B illustrate components of a bending robot 1100 according to another alternative embodiment. The bending robot 1100 in this embodiment includes a rod feeding subassembly 1104 including a rod feeding actuator 1124, a brake subassembly 1108 with a brake actuator 1146 having an integrated marking mechanism, and bending subassembly 1110 having a bending actuator 1150 including a pair of roller bearings 1154 for engaging and bending the surgical rod 1106 without notching or otherwise damaging the surgical rod 1106.

In this example, the rod feeding actuator 1124 is controlled via a feeding gear mechanism 1126, and the bending actuator 1150 is controlled via a bending gear subassembly 1152. The brake actuator 1146 is controlled by a manual clamp mechanism 1180 in this embodiment. An integrated marking mechanism, e.g., a retractable marker, may mark points on the rod which, once marked, dictate the shape of the rod as needed to correct an injury, where the marked points indicate the points of the screws along the curve of the bend. This allows for additional control over the shape of the rod, and marking ensures that the surgeon is aware entirely of which screws the rod aligns with for a spinal fusion or other procedure. Alternatively, the surgical rod could be pre-marked, e.g., every five millimeters, with a corresponding number. By displaying these numbers on the screen of a monitor viewable by the surgeon during the procedure, the surgeon can ensure proper positioning of the rods.

Figure 12:
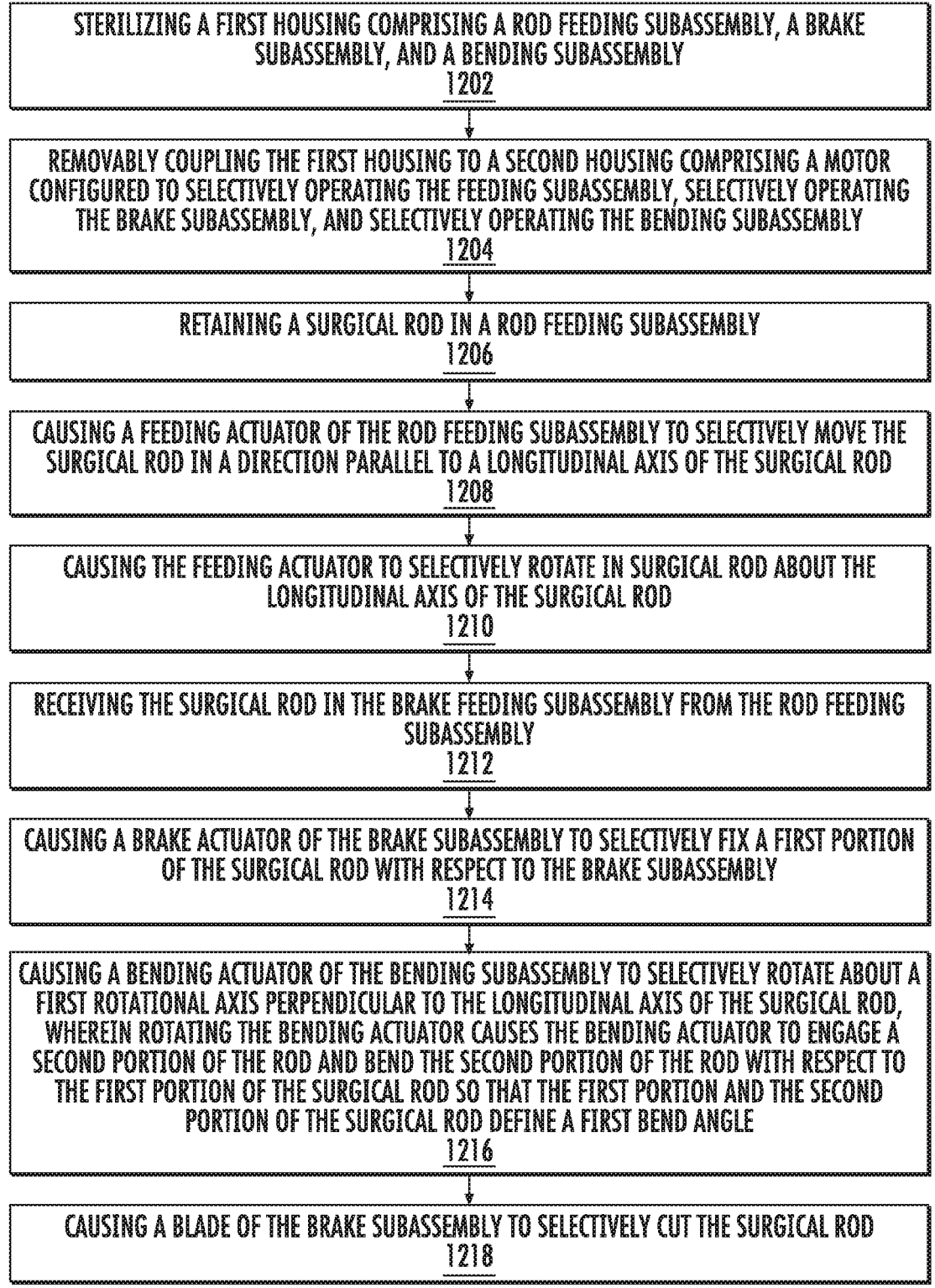
FIG. 12 is a flowchart of a method of operating a bending robot, according to some embodiment.

FIG. 12 is a flowchart of operations 1200 for operating a bending robot, according to some embodiments. The operations 1200 include sterilizing a first housing including a rod feeding subassembly, a brake subassembly, and a bending subassembly (Block 1202), and removably coupling the first housing to a second housing including a motor configured to selectively operating the rod feeding subassembly, the brake subassembly, and the bending subassembly (Block 1204). The operations 1200 further include retaining a surgical rod in the rod feeding subassembly (Block 1206), causing a feeding actuator of the rod feeding subassembly to selectively move the surgical rod in a direction parallel to a longitudinal axis of the surgical rod (Block 1208), and causing the feeding actuator to selectively rotate the surgical rod about the longitudinal axis of the surgical rod (Block 1210).

The operations 1200 further include receiving the surgical rod in the brake feeding subassembly from the rod feeding subassembly (Block 1212), and causing a brake actuator of the brake subassembly to selectively fix a first portion of the surgical rod with respect to the brake subassembly (Block 1214). The operations 1200 further include causing a bending actuator of the bending subassembly to selectively rotate about a first rotational axis perpendicular to the longitudinal axis of the surgical rod, wherein rotating the bending actuator causes the bending actuator to engage a second portion of the rod and bend the second portion of the rod with respect to the first portion of the surgical rod so that the first portion and the second portion of the surgical rod define a first bend angle. The operations 1200 further include causing a blade of the brake subassembly to selectively cut the surgical rod.

Additional operations may include data acquisition, which may occur prior to rod bending and after screws are properly placed via a camera system, which may send the data to the bending robot. Based on the data, the bending robot may perform the operations described above. In another embodiment, the data for bend points can be received through an acquisition camera and a probe that is tracked by the camera, where the probe is touched on the head of each of a plurality of pedicle screws after they have been placed on the patient's spine. Those points can be used to generate a curve that can be modified and fine-tuned by the surgeon, and that can be used to generate bend points, which can be used by the bending robot to make appropriate bends in the surgical rod. In another example, an intraoperative robot used for screw placement can be used to determine the coordinates of the pedicles and hence can be used to generate a bend curve. In some embodiments, preoperative planning software, such as Surgimap or GMAP, for example, can be used to configure the bend points, which can then be used by the bending robot to bend the surgical rod. Data from the camera may also be used to verify that the robot is operating correctly and/or within predetermined tolerances, and may generate data to instruct the robot to correct for errors in real time.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A robotic system for automatically bending a surgical rod, comprising:
   a robot base;
   rod feeding subassembly coupled to the robot base, the rod feeding subassembly comprising a feeding actuator configured to:
     retain a surgical rod therein, and
     selectively move the surgical rod in a direction parallel to a longitudinal axis of the surgical rod;
   a brake subassembly coupled to the robot base, the brake subassembly comprising a brake actuator configured to:
     receive the surgical rod from the rod feeding subassembly, and
     selectively fix a first portion of the surgical rod with respect to the brake subassembly; and
   a bending subassembly coupled to the robot base, the bending subassembly comprising a bending actuator configured to:
     selectively rotate about a first rotational axis perpendicular to the longitudinal axis of the surgical rod, wherein rotating the bending actuator causes the bending actuator to engage a second portion of the surgical rod and bend the second portion of the surgical rod with respect to the first portion of the surgical rod so that the first portion and the second portion of the surgical rod define a first bend angle
   wherein the robotic system further includes a bending robot that includes the robot base and a controlling unit, the controlling unit configured to control and monitor the operation of the bending robot,
   wherein the controlling unit further includes a controller base, a camera system, and a display device.

2. The robotic system of claim 1, wherein the rod feeding subassembly further comprises:
   a motor; and
   a feeding actuator linkage coupled between the motor and the feeding actuator, wherein the feeding actuator linkage is configured to transfer power from the motor to the feeding actuator to selectively move the surgical rod in the direction parallel to the longitudinal axis of the surgical rod.

3. The robotic system of claim 2, wherein the feeding actuator is configured to transfer power from the motor to the feeding actuator to selectively rotate the surgical rod about the longitudinal axis of the surgical rod.

4. The robotic system of claim 3, wherein the motor comprises a first motor and a second motor,
   wherein the feeding actuator linkage comprises a first feeding actuator linkage coupled between the first motor and the feeding actuator and a second feeding actuator linkage coupled between the second motor and the feeding actuator,
   wherein selective operation of the first motor in a first rotational direction and selective operation of the second motor in a second rotational direction causes the first feeding actuator linkage and the second feeding actuator linkage to move the surgical rod in a first longitudinal direction parallel to the longitudinal axis of the surgical rod.

5. The robotic system of claim 4, wherein selective operation of the first motor in a third rotational direction opposite the first rotational direction and selective operation of the second motor in a fourth rotational direction opposite the second rotational direction causes the first feeding actuator linkage and the second feeding actuator linkage to move the surgical rod in a second longitudinal direction opposite the first longitudinal direction, and
   wherein selective operation of the first motor in the first rotational direction and selective operation of the second motor in the fourth rotational direction causes the first feeding actuator linkage and the second feeding actuator linkage to rotate the surgical rod in a fifth rotational direction.

6. The robotic system of claim 3, wherein selective operation of the first motor in the third rotational direction and selective operation of the second motor in the second rotational direction causes the first feeding actuator linkage and the second feeding actuator linkage to rotate the surgical rod in a sixth rotational direction opposite the fifth rotational direction.

7. The robotic system of claim 1, wherein the brake subassembly further comprises:
   a motor; and
   a brake actuator linkage coupled between the motor and the brake actuator, wherein the brake actuator linkage is configured to transfer power from the motor to the brake actuator to selectively fix the first portion of the surgical rod with respect to the brake subassembly.

8. The robotic system of claim 7, wherein the brake subassembly further comprises a blade configured to selectively cut the surgical rod.

9. The robotic system of claim 8, wherein the brake actuator linkage is configured to transfer power from the motor to the blade to selectively cut the surgical rod.

10. The robotic system of claim 9, wherein selective operation of the motor in a first rotational direction when the brake actuator is in a neutral position causes the brake actuator linkage to move the brake actuator from the neutral position to an engaged position to selectively fix the first portion of the surgical rod with respect to the brake subassembly, and wherein selective operation of the motor in a second rotational direction opposite the first rotational direction when the brake actuator is in the engaged position causes the brake actuator linkage to move the brake actuator from the engaged position to the neutral position to selectively release the first portion of the surgical rod with respect to the brake subassembly.

11. The robotic system of claim 10, wherein selective operation of the motor in the second rotational direction when the brake actuator is in the neutral position causes the blade to cut the surgical rod.

12. The robotic system of claim 1, wherein the bending subassembly further comprises:
a motor; and
a bending actuator linkage coupled between the motor and the bending actuator, wherein the bending actuator linkage is configured to transfer power from the motor to the bending actuator to selectively rotate the bending actuator about the first rotational axis and bend the second portion of the surgical rod with respect to the first portion of the surgical rod.

13. The robotic system of claim 12, wherein the bending actuator comprises a roller bearing configured to engage the second portion of the surgical rod, wherein movement of the second portion of the surgical rod during bending causes the roller to rotate about a second rotational axis parallel to the first rotational axis.

14. The robotic system of claim 1, wherein the feeding actuator is further configured to:
after the bending actuator bends the second portion of the surgical rod with respect to the first portion of the surgical rod, selectively move the surgical rod in the direction parallel to the longitudinal axis of the surgical rod, and
selectively rotate the surgical rod about the longitudinal axis of the surgical rod, wherein the brake actuator is further configured to:
selectively fix a third portion of the surgical rod with respect to the brake subassembly, and
wherein the bending actuator is further configured to:
selectively rotate about the first rotational axis perpendicular to the longitudinal axis of the surgical rod, and
selectively rotate about the first rotational axis to bend the first portion of the surgical rod with respect to the third portion of the surgical rod so that the third portion and the first portion of the surgical rod define a second bend angle.

15. The robotic system of claim 1, further comprising a first housing comprising:
a transmission input;
a first transmission subassembly coupled between the transmission input and the feeding actuator;
a second transmission subassembly coupled between the transmission input and the brake actuator; and
a third transmission subassembly coupled between the transmission input and the bending actuator; and
a second housing comprising:
a motor; and
a transmission output configured to selectively operate in response to operating the motor, wherein the first housing is configured to engage with the second housing to couple the transmission output of the second housing to the transmission input of the first housing, wherein selectively operating the transmission output causes the transmission input to selectively transfer power from the motor to the feeding actuator, the brake actuator, and the bending actuator.

16. The robotic system of claim 15, wherein the first housing is configured to be selectively removable from the second housing.

17. The robotic system of claim 1, further comprising:
a processor circuit; and
a memory coupled to the processor circuit, the memory comprising machine-readable instructions that, when executed by the processor circuit, cause the processor circuit to:
cause the rod feeding subassembly to selectively move the surgical rod;
cause the brake subassembly to selectively fix the first portion of the surgical rod; and
cause the bending subassembly to selectively rotate about the first rotational axis to engage the second portion of the surgical rod and bend the second portion of the surgical rod with respect to the first portion of the surgical rod.

18. A method of operating a robotic system comprising:
selectively operating a rod feeding subassembly, comprising:
retaining a surgical rod in the rod feeding subassembly, and
causing a feeding actuator of the rod feeding subassembly to selectively move the surgical rod in a direction parallel to a longitudinal axis of the surgical rod;
selectively operating a brake subassembly, comprising:
receiving the surgical rod in the brake feeding subassembly from the rod feeding subassembly; and
causing a brake actuator of the brake subassembly to selectively fix a first portion of the surgical rod with respect to the brake subassembly; and
selectively operating a bending subassembly, comprising:
causing a bending actuator of the bending subassembly to selectively rotate about a first rotational axis perpendicular to the longitudinal axis of the surgical rod, wherein rotating the bending actuator causes the bending actuator to engage a second portion of the rod and bend the second portion of the rod with respect to the first portion of the surgical rod so that the first portion and the second portion of the surgical rod define a first bend angle
wherein the robotic system further includes a bending robot that includes a robot base and a controlling unit, the controlling unit configured to control and monitor the operation of the bending robot,
wherein the controlling unit further includes a controller base, a camera system, and a display device.

19. The method of claim 18, further comprising, prior to selectively operating the rod feeding subassembly, sterilizing a first housing comprising the rod feeding subassembly, the brake subassembly, and the bending subassembly; and
removably coupling the first housing to a second housing comprising a motor configured to perform the selectively operating the rod feeding subassembly, selectively operating the brake subassembly, and selectively operating the bending subassembly.

* * * * *